United States Patent
Gibson et al.

(10) Patent No.: US 7,809,444 B2
(45) Date of Patent: Oct. 5, 2010

(54) ENDOSTEAL ELECTRODE

(75) Inventors: Peter Gibson, South Coogee (AU); Ernst Lehnhardt, Hannover (DE); John L. Parker, Roseville (AU)

(73) Assignee: Cochlear Limited, Lane Cove (AU)

( * ) Notice: Subject to any disclaimer, the term of this patent is extended or adjusted under 35 U.S.C. 154(b) by 401 days.

(21) Appl. No.: 11/802,400

(22) Filed: May 22, 2007

(65) Prior Publication Data
US 2007/0282416 A1    Dec. 6, 2007

Related U.S. Application Data

(63) Continuation of application No. 10/473,925, filed as application No. PCT/AU02/00433 on Apr. 5, 2002, now abandoned.

(30) Foreign Application Priority Data

Apr. 6, 2001   (AU) .................................. PR 4259
Feb. 21, 2002  (AU) .................................. PS 0686

(51) Int. Cl.
*A61N 1/05*    (2006.01)
(52) U.S. Cl. ............................. 607/55; 607/56; 607/57; 607/136; 607/137; 607/68; 600/377; 600/379; 600/373; 600/386; 600/559
(58) Field of Classification Search .................. 607/55, 607/136–137, 56, 68; 600/377, 379, 373, 600/386, 559
See application file for complete search history.

(56) References Cited

U.S. PATENT DOCUMENTS 4,261,372 A    4/1981  Hansen et al.

(Continued)

FOREIGN PATENT DOCUMENTS

AU    2002244531    10/2002

(Continued)

OTHER PUBLICATIONS

J. Ito, et al, Tinnitus Suppression by Electrical Stimulation of the Cochlea Wall and by Cochlear Implantation: Department of Otolaryngology, Otsu Red Cross Hospital, Japan, The Laryngoscope, vol. 104 (6 Pt. 1), Jun. 1994, pp. 752-754.

(Continued)

*Primary Examiner*—Carl H Layno
*Assistant Examiner*—Natasha N Patel
(74) *Attorney, Agent, or Firm*—Kilpatrick Stockton LLP

(57) ABSTRACT

An implantable tissue-stimulating device comprising an elongate electrode carrier member (11) having a plurality of electrodes thereon. The electrodes are preferably disposed in a linear array on the carrier member (11) and are adapted to apply a preselected tissue stimulation to the cochlea. The carrier member (11) is preformed from a resiliently flexible biocompatible silicone and extends from a distal end (12) to a stop member (13). The carrier member (11) is adapted for intracochlear but extraluminar insertion within the cochlea of an implantee. In particular, the carrier member (11) is adapted to be implanted in the crevice (21) between the spiral ligament (22) and the endosteum (23) of the lateral wall of the cochlea (20). This is a quite different location to the normal placement of the cochlear implant electrode array in the scala tympani (24) of the cochlea (20). The placement of the carrier member (11) is designed to avoid any breach of the internal ducts of the cochlea (20), such as the scala tympani (24) and scala vestibuli (25) so that the normal hydrodynamic behaviour of the cochlea (20) is not affected by any intrusive device. By preserving the normal hydrodynamic behaviour of the cochlea (20), use of the carrier member (11) maximises the possibility of also preserving any hearing of the implantee that is offered by the cochlea (20). Use of the device in a system for masking or treating the symptoms of tinnitus is also described.

20 Claims, 3 Drawing Sheets

U.S. PATENT DOCUMENTS

| | | | |
|---|---|---|---|
| 4,532,930 A | | 8/1985 | Crosby et al. |
| 5,443,493 A | | 8/1995 | Byers et al. |
| 5,645,585 A | | 7/1997 | Kuzma |
| 5,795,287 A | | 8/1998 | Ball et al. |
| 5,814,095 A | | 9/1998 | Muller et al. |
| 6,070,105 A | * | 5/2000 | Kuzma ................ 607/137 |
| 6,112,124 A | | 8/2000 | Loeb |
| 6,129,753 A | | 10/2000 | Kuzma |
| 6,198,971 B1 | | 3/2001 | Leysieffer |
| 6,259,951 B1 | * | 7/2001 | Kuzma et al. ............ 607/57 |
| 6,537,700 B1 | | 3/2003 | Ovshinsky et al. |
| 6,549,814 B1 | * | 4/2003 | Strutz et al. ............ 607/137 |
| 6,565,503 B2 | | 5/2003 | Leysieffer et al. |
| 6,575,894 B2 | | 6/2003 | Leysieffer |
| 6,697,674 B2 | | 2/2004 | Leysieffer et al. |
| 7,194,314 B1 | | 3/2007 | Richter et al. |
| 7,315,763 B2 | | 1/2008 | Kuzma et al. |
| 2005/0080473 A1 | | 4/2005 | Gibson et al. |
| 2006/0079950 A1 | | 4/2006 | Lehnhardt et al. |
| 2007/0135884 A1 | | 6/2007 | Risi |

FOREIGN PATENT DOCUMENTS

| | | |
|---|---|---|
| WO | WO 90/07251 | 6/1990 |
| WO | 9631087 | 10/1996 |
| WO | WO 00/69512 | 11/2000 |
| WO | WO 02/080817 | 10/2002 |

OTHER PUBLICATIONS

M. Sakajri, et al., "A Method for Suppressing Tinnitus by Electrical Stimulation to Cochlea and Remedial Value," Research Institute for Electric Science, Hokkaido University, Sapporo Japan, Journal of the Acoustical Society of Japan (E.) vol. 14, No. 6, pp. 453-455, Nov. 1993.

W. Mckerrow, et al, "Tinnitus Suppression by Cochlear Implants," Coleman and Epstein Laboratories, Department of Otolaryngology, University of California, San Francisco, The Annals of Otology, Rhinology & Laryngology, Jul. 1991, vol. 100 (7) pp. 552-558.

International Search Report for PCT/AU02/00433, dated May 28, 2002.

AU Examiner's Report for AU 2006202622 dated Apr. 14, 2008.

International Preliminary Examination Report for PCT/AU02/00433 dated Sep. 5, 2002.

Translation of JP Notice of Reasons for Rejection for JP 2002-578856 dated Aug. 5, 2008.

* cited by examiner

US 7,809,444 B2

ENDOSTEAL ELECTRODE

CROSS-REFERENCE TO RELATED APPLICATIONS

This application is a continuation of U.S. patent application Ser. No. 10/473,925, filed on Dec. 10, 2004, entitled, "Endosteal Electrode," which is a national stage application of PCT/AU2002/000433 filed Apr. 5, 2002, which claims priority from Australian Application No. PR 4259 filed Apr. 6, 2001, and Australian Application No. PS 0686.

FIELD OF THE INVENTION

The present invention relates to an auditory prosthesis adapted for intracochlear but extraluminar placement within the cochlea. An application of the device for masking or treating tinnitus is also described.

BACKGROUND OF THE INVENTION

Hearing loss, which may be due to many different causes, is generally of two types, conductive and sensorineural. In some cases, a person may have hearing loss of both types. Of them, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells.

In many people who are profoundly deaf, however, the reason for their deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, no matter how loud the acoustic stimulus is made, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532, 930, the contents of which are incorporated herein by reference, provides a description of one type of traditional cochlear implant system.

Typically, cochlear implant systems have consisted of essentially two components, an external component commonly referred to as a processor unit and an internal implanted component commonly referred to as a receiver/stimulator unit. Traditionally, both of these components have cooperated together to provide the sound sensation to a user.

The external component has traditionally consisted of a microphone for detecting sounds, such as speech and environmental sounds, a speech processor that converts speech into a coded signal, a power source such as a battery, and an external transmitter coil.

The coded signal output by the sound processor is transmitted transcutaneously to the implanted receiver/stimulator unit situated within a recess of the temporal bone of the user. This transcutaneous transmission occurs via the external transmitter coil which is positioned to communicate with an implanted receiver coil provided with the stimulator/receiver unit. This communication serves two essential purposes, firstly to transcutaneously transmit the coded sound signal and secondly to provide power to the implanted receiver/stimulator unit. Conventionally, this link has been in the form of a radio frequency (RF) link, but other such links have been proposed and implemented with varying degrees of success.

The implanted receiver/stimulator unit traditionally includes a receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

Traditionally, at least the speech processor of the external componentry has been carried on the body of the user, such as in a pocket of the user's clothing, a belt pouch or in a harness, while the microphone has been mounted on a clip mounted behind the ear or on the lapel of the user.

More recently, due in the main to improvements in technology, the physical dimensions of the sound processor have been able to be reduced allowing for the external componentry to be housed in a small unit capable of being worn behind the ear of the user. This unit allows the microphone, power unit and the sound processor to be housed in a single unit capable of being discretely worn behind the ear, with the external transmitter coil still positioned on the side of the user's head to allow for the transmission of the coded sound signal from the sound processor and power to the implanted stimulator unit.

It is further envisaged that with continual improvements in technology all the traditional external componentry may be implanted in the user. In such a system all of the speech processing may be performed inside the implanted stimulator unit, via an implanted microphone.

It is known in the art that the cochlea is tonotopically mapped. In other words, the cochlea can be partitioned into regions, with each region being responsive to signals in a particular frequency range. This property of the cochlea has been exploited by providing the electrode assembly with an array of electrodes, each electrode being arranged and constructed to deliver a stimulating signal within a preselected frequency range, to the appropriate region within the scala tympani of the cochlea. The electrical currents and electric fields from each electrode stimulate the nerves disposed on the modiolus of the cochlea.

Despite the enormous benefits offered by cochlear implants, one potential disadvantage of placement of the electrode assembly within the scala tympani is that it is necessary to breach the internal ducts of the cochlea, generally the scala tympani. The breaching of the scala tympani of the cochlea adversely affects the hydrodynamic behaviour of the cochlea and is thought to prevent or at least reduce any chance of preservation of any residual hearing of the implantee. This can be problematic for those persons who would benefit from use of a cochlear implant to improve hearing of relatively high frequencies but who have some residual hearing of relatively low frequencies. In such a case, the implantee is forced to trade off an existing residual capacity to hear relatively low frequency sounds against the desirability of being able to have a hearing sensation of relatively high frequency sounds offered by a cochlear implant.

There have been a number of proposals put forward to provide a hybrid system whereby a cochlear implant system can be used in conjunction with residual hearing, usually assisted by the use of a hearing aid. One such example of a proposed system is described in International Patent Application No WO 00/69512. In this application, the hybrid system utilises a hearing aid to amplify the low frequency sound enabling the user to rely on normal hearing processes to experience such sounds. For high frequency sounds, the hybrid system utilises a relatively conventional cochlear stimulation device consisting of a short cochlear electrode array. The short cochlear electrode array of this application is described as consisting of 4-8 electrodes and is inserted directly through the round window membrane making contact with the basal region of the cochlea. Therefore the system as described in this application still uses a relatively obtrusive electrode array making it very difficult to preserve any residual hearing the patient may have in such areas.

As already described, the present application is also directed to a device for masking or treating tinnitus. Tinnitus is the medical term for a condition in which sufferers report a ringing in their ears or head when there is in fact no external sound present in the sufferer's audible range. Although some people hear a ringing noise, others report the noise as being a hissing, a chirping, or a clicking. There are various estimates as to how many sufferers of tinnitus there are worldwide. For example, it is suggested that some 50 million Americans suffer from tinnitus, with about 83% of them hearing a constant ringing. Other figures suggest at least 12 million people have tinnitus to what is regarded as a distressing degree.

For some people, tinnitus is just a nuisance. For others, it can be a quite debilitating condition. Usually, the only relief tinnitus sufferers will experience is an occasional reduction in the loudness of the tinnitus from time to time.

The cause of tinnitus or at least its onset is unclear. There is, however, data available that demonstrates that exposure to loud noise is a trigger for the condition. Other suggested triggers include severe head trauma, certain medications, sinus and respiratory infections, ear infections, wax build-up and certain types of tumours.

There are, as yet, no cures for tinnitus but there are several treatments currently used to provide at least some relief. One treatment is the use of what are commonly referred to as tinnitus maskers. One example of a tinnitus masker is disclosed in PCT Patent Application WO 90/07251. Tinnitus maskers are essentially small battery operated devices which are worn like a hearing aid behind or in the ear, and cover (mask) the tinnitus psychoacoustically by artificial sounds which are emitted, for example, via a hearing aid speaker into the auditory canal and which reduce the disturbing tinnitus as far as possible below the threshold of perception. The artificial sounds are often narrowband noise (for example, third octave noise) which in its spectral position and its loudness level can be adjusted via a programming device to enable the maximum position adaptation to the individual tinnitus situation. This form of treatment is available in several forms and when properly administered, has been demonstrated to assist in somewhere between 58% and 65% of cases. Masking is simply the addition of an outside sound that serves as a substitute or mask for the tinnitus.

Masking systems known to date are typically worn within the ear canal or positioned nearby so as to ensure provision of a masking sound to the sufferer and as a result these devices stigmatise the wearer and are worn reluctantly.

Implantable tinnitus maskers are known, such as that described in U.S. Pat. No. 5,795,287. Such devices utilise electromechanical transducers coupled to the ossicular chain to produce the artificial masking sounds, however, these devices require a very complicated surgery to implant as the electromechanical transducer must mechanically manipulate the ossicular chain. Also, it has been found that such mechanical coupling is not always guaranteed to be stable as pressure necroses in the area of the middle ear ossicle has been found to occur in a number of cases resulting in bone erosion.

The present invention relates to a new system for treating the symptoms of tinnitus that preferably does not require complicated surgery nor the fixation of electromechanical transducers to the ossicles.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present invention is firstly directed to an implant that can be inserted in the cochlea but in a position external to the scala tympani. Such an implant provides an alternative option for those persons described above who would benefit from the use of a cochlear implant to improve hearing of relatively high frequencies but who have some residual hearing of relatively low frequencies. The present invention further preferably aims to provide a cochlear implant system that preserves the normal hydrodynamic nature of the cochlea allowing for an electrode array to be positioned to stimulate the desired neurons without causing damage to the important internal ducts of the cochlea.

The present invention is secondly directed to an implant, as described above, that can be used as a means of masking the symptoms of tinnitus.

According to a first aspect, the present application is directed to a first invention comprising an implantable tissue-stimulating device having a carrier member having at least one electrode thereon, the carrier member being adapted for intracochlear but extraluminar insertion within the cochlea of an implantee.

According to a second aspect, the present invention is directed to a second invention comprising an implantable tissue-stimulating device for use in the masking or treatment of the symptoms of tinnitus, the device having a carrier member having at least one electrode thereon, the carrier member being adapted for intracochlear but extraluminar insertion within the cochlea of an implantee.

According to a third aspect, the present invention is directed to a third invention comprising an implantable tissue-stimulating device when used in the masking or treatment of the symptoms of tinnitus, the device having a carrier member having at least one electrode thereon, the carrier member being adapted for intracochlear but extraluminar insertion within the cochlea of an implantee.

In the above aspects, the device can be a cochlear implant. In one embodiment, the carrier member can be a cochlear implant carrier member. The carrier member preferably has a body having a plurality of electrodes mounted thereon. The electrodes can be disposed in an array on the carrier member. The electrodes can be adapted to apply a preselected tissue stimulation.

In a preferred embodiment, the carrier member is adapted to be implanted in a crevice between the spiral ligament and the endosteum of the lateral wall of the cochlea. This is quite different to the normal placement of the electrode array of a traditional cochlear implant in the scala tympani of the cochlea.

The placement of the device is preferably designed to avoid any breach of the internal ducts of the cochlea (eg. scala tympani and scala vestibuli) so that the normal hydrodynamic behaviour of the cochlea is not affected by any intrusive device. This is important, as for implantees suffering tinnitus, use of the device does not lead to loss of what otherwise may be good hearing. For implantees with at least some sensorineural hearing loss, use of the device maximises the possibility of also preserving residual hearing offered by the implantee's cochlea. In this case, it is envisaged that use of the device will have particular benefit in those instances where the implantee has substantial residual hearing in the low frequencies but would benefit from supplemental stimulation in a relatively higher frequency range. In this case, the implantee may benefit from use of a hearing aid that amplifies the relatively low frequencies still detectable by the implantee and a cochlear implant for detection of relatively high frequencies.

In a preferred embodiment, the carrier member has a maximum length of about 7-10 mm, a width of about 0.6 mm and a thickness no greater than about 0.2 mm and, more preferably, about 0.1 mm. In a further embodiment, the carrier member can have an inner surface and an outer surface, the inner surface being adapted to face inwardly into the cochlea, while the outer surface faces toward the endosteum of the cochlea. In one embodiment, the inner face can have a concavity. In a further embodiment, the outer face can have a convexity.

In a further embodiment, the thickness of the carrier member between its inner surface and outer surface can be substantially constant for at least a majority of its length from the proximal end to the distal end. In another embodiment, the thickness of the carrier can change, such as decrease, from the proximal end to the distal end. In a preferred embodiment, the carrier can be relatively more resiliently flexible in a longitudinal plane and relatively less resiliently flexible in a lateral plane.

The carrier member can be relatively flexible and preferably adapted to follow the curvature of the endosteum along the basal turn. In a preferred embodiment, a proximal end of the carrier member can be identified by a stop member. The stop member can extend substantially at right angles to the longitudinal axis of the carrier member. The stop member preferably has a length of between about 1.5 and 2.0 mm.

The stop member can serve as both a region for grasping the carrier member and also act to prevent insertion of the carrier member within the crevice beyond a predetermined maximum depth.

In a still further embodiment, said at least one electrode has a surface that is at least adjacent the inner surface of the carrier. More preferably, each of the electrodes in the array has a surface that is adjacent the inner surface of the carrier member. In a further embodiment, the surfaces of the electrodes are aligned with the inner surface of the carrier member. In another embodiment, the surfaces of the electrodes stand proud of the inner surface of the carrier member. It is also envisaged that the electrode surface could also be recessed into the inner surface of the carrier member.

In one embodiment, the carrier member can be formed from a biocompatible elastomeric material. In one embodiment, the elastomeric material can be a silicone rubber. In another embodiment, the carrier member can be formed from a biocompatible polyurethane or similar material.

The surfaces of the carrier member are preferably smooth to prevent any damage to the cochlea as the array is placed in the cochlea.

In a preferred embodiment, the electrode array can include electrically conducting wires connected to the electrodes and extending to at least said proximal end. In one embodiment, one wire can be connected to each of said electrodes. In another embodiment, at least two wires can be connected to each of said electrodes.

Each electrode can comprise a contact element. The carrier member can have a longitudinal axis with each contact element arranged orthogonally to the longitudinal axis. The contact elements can be formed from a biocompatible material. The biocompatible material of the contact element can be platinum. The wires may preferably be connected to the contact elements by welding, or any other suitable connecting method.

Once implanted, the electrodes of the carrier member preferably receive stimulation signals from a stimulator means. The stimulator means is preferably electrically connected to the carrier member by way of an electrical lead. The lead can include the one or more wires extending from each electrode of the array mounted on the carrier member.

In one embodiment, the lead can extend from the carrier member to the stimulator means or at least the housing thereof. In one embodiment, the lead is continuous with no electrical connectors, at least external the housing of the stimulator means, required to connect the wires extending from the electrodes to the stimulator means. One advantage of this arrangement is that there is no requirement for the surgeon implanting the device to make the necessary electrical connection between the wires extending from the electrodes and the stimulator means.

The stimulator means is preferably positioned within a housing that is implantable within the implantee. The housing for the stimulator means is preferably implantable within a recess in the bone behind the ear posterior to the mastoid.

When implanted, the housing preferably contains, in addition to the stimulator means, a receiver means. The receiver means is preferably adapted to receive signals from a controller means. The controller means is, in use, preferably mounted external to the body of the implantee such that the signals are transmitted transcutaneously through the skin of the implantee.

Signals can preferably travel from the controller means to the receiver means and vice versa. The receiver means can include a receiver coil adapted to receive radio frequency (RF) signals from a corresponding transmitter coil worn externally of the body. The radio frequency signals can comprise frequency modulated (FM) signals. While described as a receiver coil, the receiver coil can preferably transmit signals to the transmitter coil which receives the signals.

The transmitter coil is preferably held in position adjacent the implanted location of the receiver coil by way of respective attractive magnets mounted centrally in, or at some other position relative to, the coils.

The external controller can comprise a processor adapted to output one or more stimulation regimes to the stimulator.

Where the device is being used to mask or treat the symptoms of tinnitus, the external controller can comprise a processor adapted to output one or more stimulation regimes to the stimulator.

In one embodiment of this application, the stimulation regime can comprise a random continuous sub-threshold stimulation regime. In this regime, the stimulation signals output to the electrodes of the carrier member are at a level below the threshold of hearing of the sufferer.

In another embodiment, the stimulation regime can comprise a random continuous supra-threshold stimulation, such as white noise.

In a still further embodiment, the stimulation regime can comprise a random discontinuous supra-threshold stimulation regime. It is postulated by the present inventors that irregular stimulation may be sufficient to reduce the impact of the tinnitus condition. Irregular stimulation also has the advantage of being relatively power-efficient and hence would result in longer battery life for the device.

In yet a further embodiment, the stimulation regime can comprise a treatment-on-demand regime. Such a regime is postulated by the present inventors as being advantageous for those persons who only suffer irregular episodes of tinnitus. In this embodiment, the external controller can further comprise an activation means. The activation means can comprise a switch means on the external controller. In this case, the sufferer or a third person could activate the processor when required.

Where the device is being used to provide a hearing sensation, the external controller preferably comprises a speech processor adapted to receive signals output by a microphone. During use, the microphone is preferably worn on the pinna of the implantee, however, other suitable locations can be envisaged, such as the lapel of the implantee's clothing. The speech processor encodes the sound detected by the microphone into a sequence of electrical stimuli following given algorithms, such as algorithms already developed for cochlear implant systems. The encoded sequence is transferred to the implanted receiver/stimulator means using the transmitter and receiver coils. The implanted receiver/stimulator means demodulates the modulated FM signal and allocates the electrical pulses to the appropriate attached electrode by an algorithm which is consistent with the chosen speech coding strategy.

In one embodiment, the processor can be adapted to receive signals from the microphone when external sounds, such as speech, are present and to output a stimulation regime, when no external sounds are present, that is adapted to mask or treat the symptoms of tinnitus.

The external controller preferably further comprises a power supply. The power supply can comprise one or more rechargeable batteries. The transmitter and receiver coils are used to provide power via transcutaneous induction to the implanted receiver/stimulator means and the electrode array.

While the implant system can rely on external componentry, in another embodiment, the controller means, including the microphone where present, the processor, and the power supply can also be implantable. In this embodiment, the controller means can be contained within a hermetically sealed housing or the housing used for the stimulator means.

An implantable controller means also preferably has an activation means that provides the implantee or a third person with a means to activate a stimulation regime when required. In one embodiment, the inactivation means can comprise a magnetic switch. In this case, the implantable controller means would preferably incorporate a magnetic field detector which is triggered on detecting the presence of a suitable magnet held close to the location of the implantable controller.

In another embodiment, the activation means can comprise a radio frequency switch means. In this case, the implantable controller can include a radio frequency detector means adapted to receive a particular pre-determined or programmed signal from a radio transmitter. The radio transmitter is activated when required by the implantee or a third person.

In yet another embodiment, the activation means can comprise an infrared switch means. In this case, the implantable controller can include a infrared detector means adapted to receive a particular pre-determined or programmed infrared signal from a infrared transmitter. The infrared transmitter is activated when required by the implantee or a third person.

According to a fourth aspect, the present invention is directed to a fourth invention comprising a method of inserting a tissue-stimulating device as defined above into a cochlea of an implantee the method comprising the steps of:

performing a fenestration to access the crevice of the cochlea between the spiral ligament and the endosteum of the lateral wall of the cochlea;

placing the device in the crevice; and closing the fenestration.

According to a fifth aspect, the present invention is directed to a fifth invention comprising a method of treating the symptoms of tinnitus comprising inserting a device as defined above into a cochlea of an implantee, the method comprising the steps of:

performing a fenestration to access the crevice of the cochlea between the spiral ligament and the endosteum of the lateral wall of the cochlea;

placing the device in the crevice; and closing the fenestration.

In a preferred embodiment of the fourth and fifth aspects, the device is guided very gently through the fenestration and into the crevice.

Following placement of the device, the method can include the step of covering the fenestration with soft body tissue and/or bony dust mixed with fibrin.

Once in place, the device can be used to output one or more stimulation regimes to the cochlea to provide a hearing sensation and/or mask or treat the symptoms of tinnitus as described above.

BRIEF DESCRIPTION OF THE DRAWINGS

By way of example only, a preferred mode of carrying out the invention is described with reference to the accompanying drawings, in which.

PREFERRED MODE OF CARRYING OUT THE INVENTION

Figure 1:
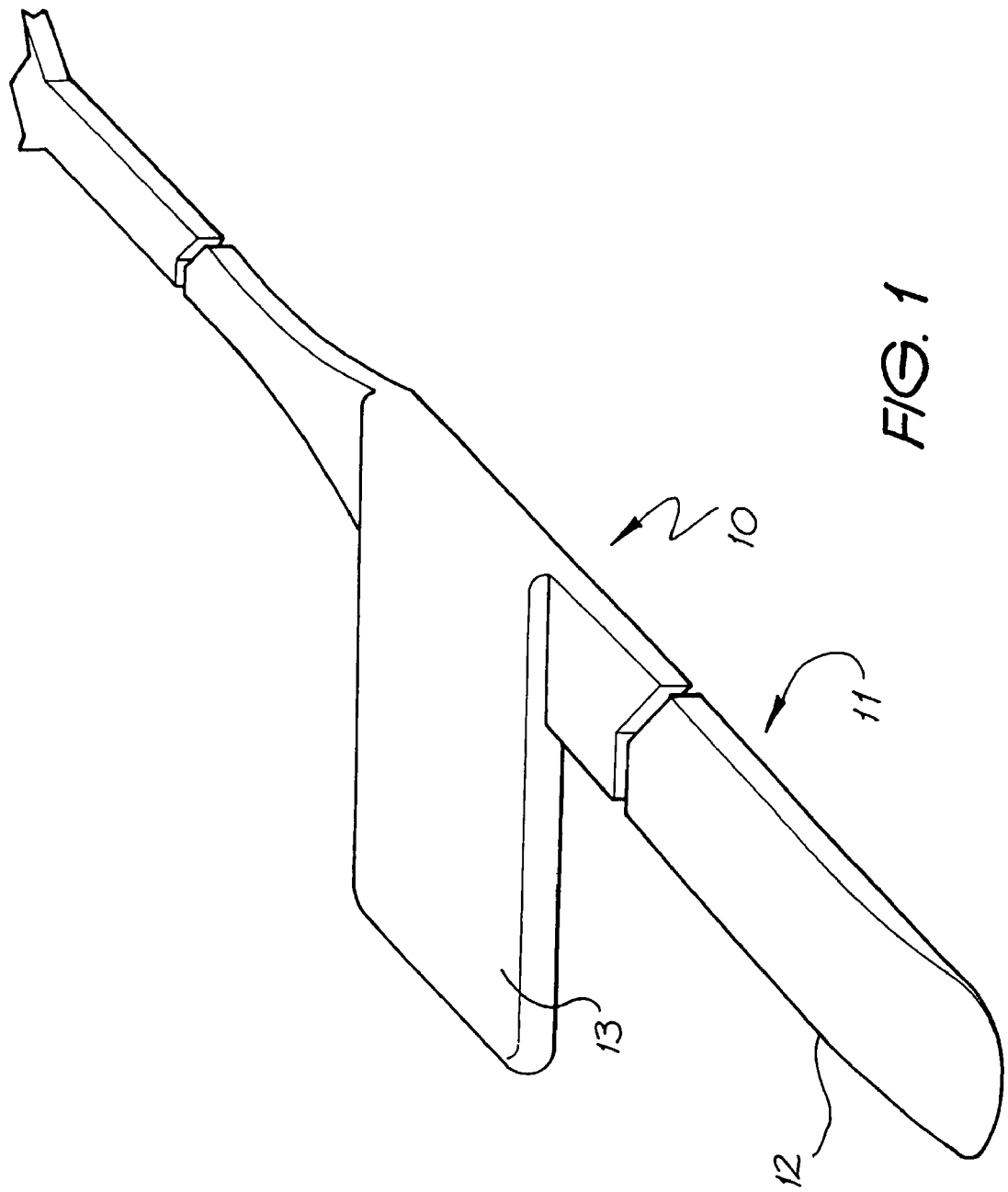
FIG. 1 is a perspective view of one embodiment of a carrier member of an implantable electrode array according to the present invention.

One embodiment of an electrode assembly for use in the present invention according to the present invention is depicted generally as 10 in the drawings.

The assembly 10 includes an elongate electrode carrier member 11. For the purposes of clarity, the plurality of electrodes that are mounted on the carrier member 11 are not depicted in the drawings. While not depicted, the electrodes can be disposed in a linear array on the carrier member 11 and be adapted to apply a preselected tissue stimulation to the cochlea.

The depicted carrier member 11 is preformed from a resiliently flexible biocompatible silicone and extends from a distal end 12 to a stop member 13.

The carrier member 11 is adapted for intracochlear but extraluminar insertion within the cochlea of an implantee.

Figure 2:
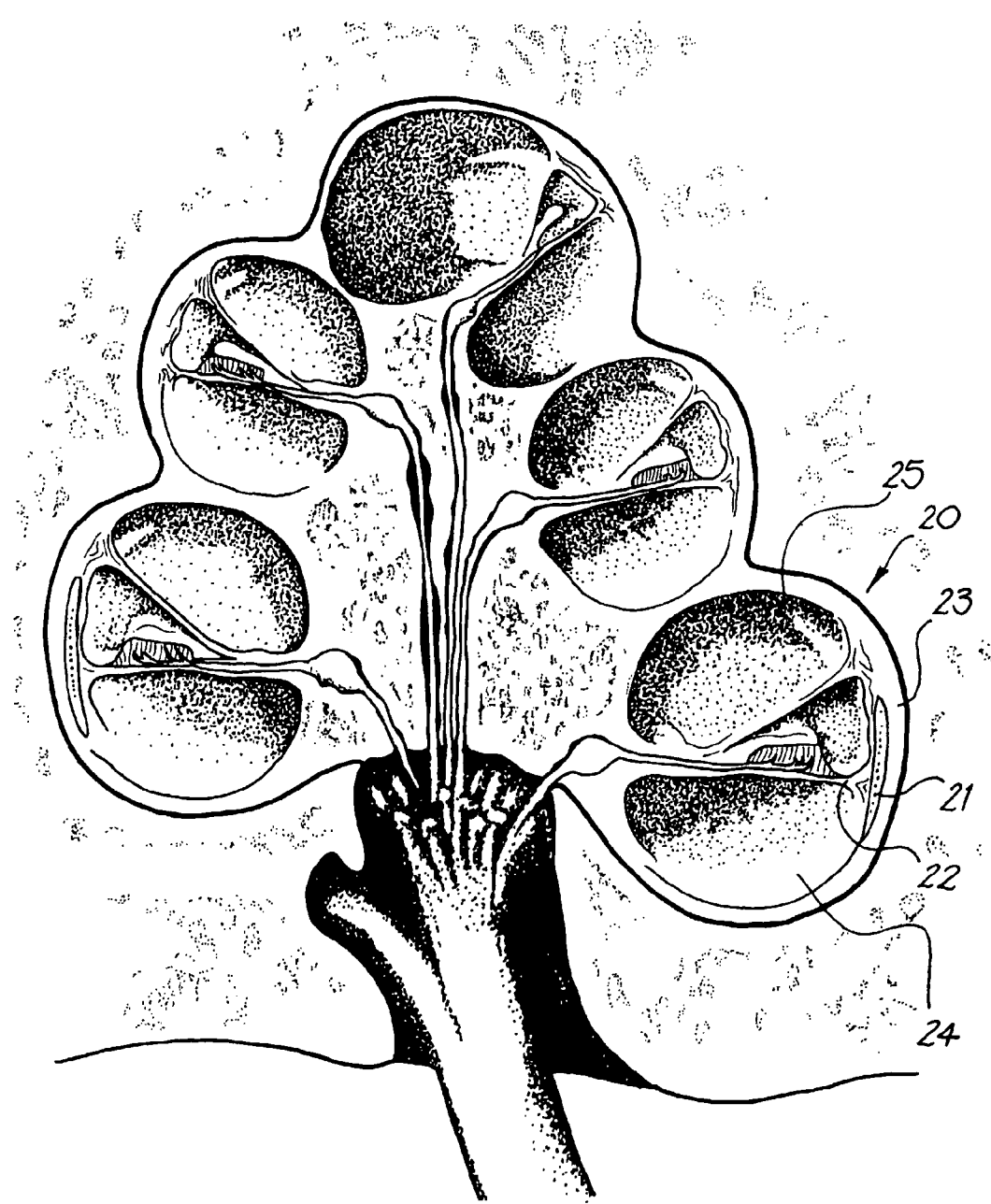
FIG. 2 is a cross-sectional view through a human cochlea depicting the desired position for placement of the electrode array according to the present invention.
Figure 3:
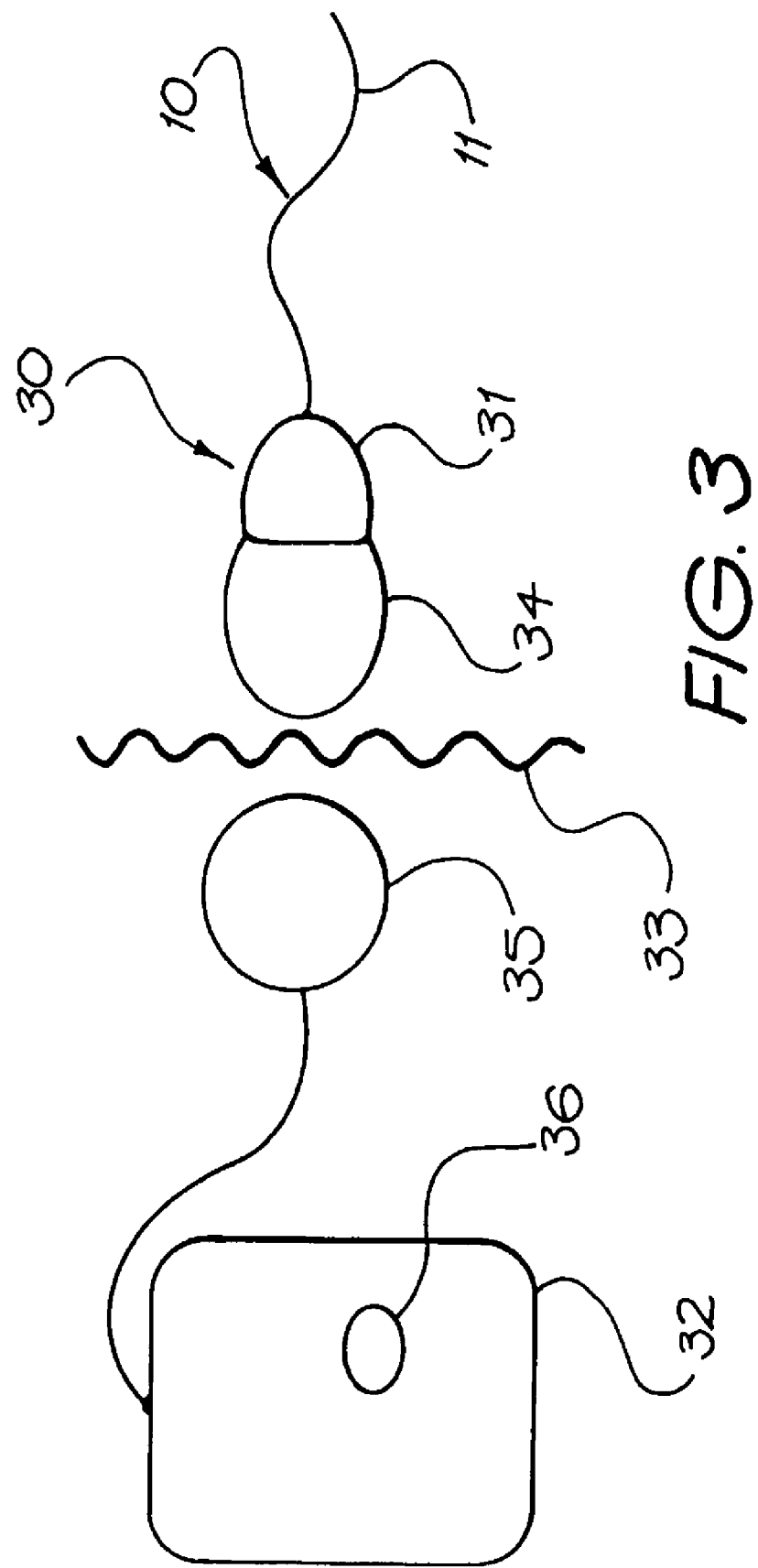
FIG. 3 is a pictorial representation of one embodiment of a system that can utilise the carrier member of FIG. 1 whether it be for providing a hearing sensation to an implantee and/or to mask or treat the symptoms of tinnitus.

In use, the carrier member 11 is adapted to be implanted in the crevice 21 (see FIG. 2) between the spiral ligament 22 and the endosteum 23 of the lateral wall of the cochlea 20. This is a quite different location to the normal placement of the cochlear implant electrode array in the scala tympani 24 of the cochlea 20.

The placement of the carrier member 11 is designed to avoid any breach of the internal ducts of the cochlea 20 (eg. scala tympani 24 and scala vestibuli 25) so that the normal hydrodynamic behaviour of the cochlea 20 is not affected by any intrusive device. By preserving the normal hydrodynamic behaviour of the cochlea 20, use of the carrier member 11 maximises the possibility of also preserving any hearing of the implantee that is offered by the cochlea 20.

In the depicted embodiment, the carrier member 11 has a maximum length of about 8-10 mm, a width of about 0.6 mm and a thickness no greater than about 0.1 mm. The thickness of the carrier member between its inner surface and outer surface is substantially constant for at least a majority of its length from the distal end 12 to the stop member 13, except in the region adjacent the end 12 where the thickness gradually tapers towards end 12.

The depicted carrier 11 is more resiliently flexible in a longitudinal plane and relatively less resiliently flexible in a lateral plane. The carrier member 11 is adapted to follow the curvature of the endosteum along the basal turn of the cochlea 20.

As depicted, the stop member 13 extends substantially at right angles to the longitudinal axis of the carrier member 11. The depicted stop member 13 has a length of between about 1.5 and 2.0 mm.

The stop member 13 serves as both a region for grasping the carrier member 11 and also acts to prevent insertion of the carrier member 11 within the crevice 21 beyond a predetermined maximum depth (eg. 8-10 mm).

While not depicted, the electrode assembly 10 includes electrically conducting wires connected to the electrodes and extending at least beyond the stop member 13. In the depicted embodiment, one wire can be connected to each of said electrodes.

In use, a surgeon would perform a fenestration to access the crevice 21 between the spiral ligament 22 and the endosteum 23 of the lateral wall of the cochlea 20. The carrier member 11 would then be inserted into the crevice 21 using an insertion tool that grips the stop member 13 and guides the carrier member 11 very gently into the crevice 21. Once positioned, the surgeon could close the fenestration by covering it with soft body tissue and/or bony dust mixed with fibrin.

Once implanted, the electrodes of the carrier member 11 receive stimulation signals from an implantable stimulator 30.

The stimulator 30 is positioned within a housing 31 that is implantable within the implantee. The housing 31 for the stimulator 30 is implantable within a recess in the bone behind the ear posterior to the mastoid.

When implanted, the housing 31 contains, in addition to the stimulator 30, a receiver. The receiver is adapted to receive signals from a controller 32. The controller 32 is, in use, typically mounted external to the body 33 of the implantee such that the signals are transmitted transcutaneously through the skin of the implantee. The controller 32 can be worn on the body of the user or can be adapted to be worn behind the ear of the user in much the same way as conventional hearing aid devices.

The signals travel from the controller 32 to the receiver and vice versa by use of a receiver coil 34 adapted to receive radio frequency (RF) signals from a corresponding transmitter coil 35 worn externally of the body 33. The radio frequency signals can comprise frequency modulated (FM) signals. While described as a receiver coil, the receiver coil 34 can also transmit signals to the transmitter coil 35 which receives the signals.

The transmitter coil 35 is held in position adjacent the implanted location of the receiver coil 34 by way of respective attractive magnets mounted centrally in, or at some other position relative to, the coils.

The external controller 32 comprises a processor adapted to output one or more stimulation regimes to the stimulator 31. It is also envisaged that the stimulator 31 may have the capability to store one or more stimulation regimes and upon request deliver the regime to the user via the electrodes.

In one use of the system, the stimulation regimes of the stimulator 31 are designed to mask or treat the symptoms of tinnitus. In one embodiment, the stimulation regime can comprise a random continuous sub-threshold stimulation regime. In this regime, the stimulation signals output to the electrodes of the carrier member 11 are at level below the threshold of hearing of the sufferer.

In another embodiment, the stimulation regime can comprise a random continuous supra-threshold stimulation, such as white noise.

In a still further embodiment, the stimulation regime can comprise a random discontinuous supra-threshold stimulation regime.

In yet a further embodiment, the stimulation regime can comprise a treatment-on-demand regime. In this embodiment, the external controller 32 can further comprise an activation means 36. The depicted activation means 36 comprises a switch on the external controller 32. In this case, the sufferer or a third person could activate the processor when required.

In addition to the above, the processor can be adapted to receive signals output by a microphone (not depicted). In this case and during use, the microphone can be worn on the pinna of the implantee, however, other suitable locations can be envisaged, such as a lapel of the implantee's clothing. In this case, the processor can encode the sound detected by the microphone into a sequence of electrical stimuli following given algorithms, such as algorithms already developed for cochlear implant systems. The encoded sequence is then transferred to the implanted stimulator 30 using the transmitter and receiver coils. The implanted stimulator 30 demodulates the FM signals and allocates the electrical pulses to the appropriate attached electrode by an algorithm which is consistent with the chosen speech coding strategy.

The housing of the external controller 32 further houses a power supply. In the depicted embodiment, the power supply comprise one or more rechargeable batteries. The transmitter and receiver coils are used to provide power via transcutaneous induction to the implanted stimulator 30 and the electrode array 10.

While the implant system can rely on external componentry, in another embodiment, the controller, including the microphone where present, the processor, and the power supply can also be implantable. In this embodiment, which is not depicted, the controller can be contained within a hermetically sealed housing or the housing used for the stimulator.

An implantable controller means would typically have an activation means that provides the implantee or a third person with a means to activate a stimulation regime when required. In one embodiment, the inactivation means can comprise a magnetic switch. In this case, the implantable controller would preferably incorporate a magnetic field detector which is triggered on detecting the presence of a suitable magnet held close to the location of the implantable controller.

In another embodiment, the activation means can comprise a radio frequency switch means. In this case, the implantable controller can include a radio frequency detector means adapted to receive a particular pre-determined or programmed signal from a radio transmitter. The radio transmitter is activated when required by the implantee or a third person.

In yet another embodiment, the activation means can comprise an infrared switch means. In this case, the implantable controller can include a infrared detector means adapted to receive a particular pre-determined or programmed infrared signal from a infrared transmitter. The infrared transmitter is activated when required by the implantee or a third person.

The present invention provides an implantable device that can be used to provide a hearing sensation to an implantee with sensorineural hearing loss and/or mask or treat the symptoms of tinnitus while preserving the hearing of the implantee's cochlea into which the stimulating electrode array has been inserted.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An endosteal electrode array configured to be implanted into a crevice formed in a recipient's cochlea outside of the cochlea's internal ducts comprising:
    an elongate carrier member having a longitudinal axis and having an inner concave surface and an outer convex surface, and wherein the carrier member has a width that is at least twice as great as a thickness of the carrier member;
    a plurality of electrodes mounted on the carrier member such that at least one surface of each of the plurality of electrodes is adjacent to the inner concave surface; and
    a substantially planar stop member disposed at the proximal end of the carrier member, wherein a planar surface of the stop member is generally parallel to the longitudinal axis of the carrier member.

2. The electrode array of claim 1, wherein the plurality of electrodes is configured to apply a preselected tissue stimulation.

3. The electrode array of claim 1, wherein the width is about 0.6 mm and the thickness is about 0.1 mm to 0.2 mm.

4. The electrode array of claim 1, wherein the carrier member is configured such that the carrier member may be implanted into the crevice such that the inner concave surface faces toward the internal ducts of the cochlea.

5. The electrode array of claim 1, wherein the inner concave and outer convex surfaces are smooth.

6. The electrode array of claim 1, wherein the at least one surface of each of the plurality of electrodes is aligned with the inner concave surface.

7. An endosteal electrode array configured to be implanted into a crevice formed in a recipient's cochlea outside of the cochlea's internal ducts comprising:
    a carrier member having a longitudinal axis, wherein the carrier member is relatively more resiliently flexible in a longitudinal plane and relatively less resiliently flexible in a lateral plane, and wherein the carrier member has a width that is at least twice as great as a thickness of the carrier member;
    a plurality of electrodes mounted on the carrier member such that at least one surface of each of the plurality of electrodes is adjacent to an inner surface of the carrier member; and
    a substantially planar stop member disposed at the proximal end of the carrier member, wherein a planar surface of the stop member is generally parallel to the longitudinal axis of the carrier member.

8. The electrode array of claim 7, wherein the plurality of electrodes is configured to apply a preselected tissue stimulation.

9. The electrode array of claim 7, wherein the width is about 0.6 mm and the thickness is about 0.1 mm to 0.2 mm.

10. The electrode array of claim 7, wherein the inner surface of the carrier member is concave and an outer surface of the carrier member is convex.

11. The electrode array of claim 10, wherein the carrier member is configured such that carrier member may be implanted into the crevice such that the inner surface faces toward the internal ducts of the cochlea.

12. The electrode array of claim 10, wherein the inner concave and outer surfaces are smooth.

13. The electrode array of claim 10, wherein the at least one surface of each of the plurality of electrodes is aligned with the concave inner surface.

14. A hearing prosthesis comprising:
    an endosteal electrode array configured to be implanted into a crevice formed in a recipient's cochlea outside of the cochlea's internal ducts comprising:
        an elongate carrier member having a longitudinal axis and having an inner concave surface and an outer convex surface, and wherein the carrier member has a width that is at least twice as great as a thickness of the carrier member;
        a plurality of electrodes mounted on the carrier member such that at least one surface of each of the plurality of electrodes is adjacent to the inner concave surface; and
        a substantially planar stop member disposed at the proximal end of the carrier member, wherein a planar surface of the stop member is generally, parallel to the longitudinal axis of the carrier member.

15. The hearing prosthesis of claim 14, further comprising: a signal processor for processing sounds into stimuli.

16. The hearing prosthesis of claim 15, further comprising an implanted stimulator connected to the electrode array and in communication with the signal processor.

17. The hearing prosthesis of claim 15, wherein the carrier member is configured such that the carrier member may be implanted into the crevice such that the inner concave surface faces toward the internal ducts of the cochlea.

18. The hearing prosthesis of claim 15, wherein the carrier member is relatively more resiliently flexible in a longitudinal plane and relatively less resiliently flexible in a lateral plane.

19. The hearing prosthesis of claim 15, wherein the inner concave and outer convex surfaces are smooth.

20. The hearing prosthesis of claim 15, wherein the at least one surface of each of the plurality of electrodes is aligned with the inner concave surface.

* * * * *